US011614623B2

(12) United States Patent
Padula et al.

(10) Patent No.: US 11,614,623 B2
(45) Date of Patent: Mar. 28, 2023

(54) HOLOGRAPHIC REAL SPACE REFRACTIVE SYSTEM

(71) Applicant: Veyezer, LLC, Guilford, CT (US)

(72) Inventors: William V. Padula, Killingworth, CT (US); Teddi R. Dinsmore, Killingworth, CT (US)

(73) Assignee: Veyezer, LLC, Killingworth, CT (US)

( * ) Notice: Subject to any disclaimer, the term of this patent is extended or adjusted under 35 U.S.C. 154(b) by 449 days.

(21) Appl. No.: 16/923,672

(22) Filed: Jul. 8, 2020

(65) Prior Publication Data

US 2020/0409153 A1 Dec. 31, 2020

Related U.S. Application Data

(63) Continuation-in-part of application No. 16/593,619, filed on Oct. 4, 2019, now Pat. No. 11,253,149, which
(Continued)

(51) Int. Cl.
*G02B 27/01* (2006.01)

(52) U.S. Cl.
CPC .. *G02B 27/0172* (2013.01); *G02B 2027/0174* (2013.01); *G02B 2027/0187* (2013.01)

(58) Field of Classification Search
CPC ......... A61B 3/028; A61B 3/032; A61B 3/103; G02B 27/0172; G02B 2027/0174; G02B 2027/0187
(Continued)

(56) References Cited

U.S. PATENT DOCUMENTS 5,491,492 A 2/1996 Knapp et al.
9,101,312 B2 8/2015 Walderf et al.
(Continued)

FOREIGN PATENT DOCUMENTS

CN 105662334 B 7/2017
CN 107260505 A 10/2017
(Continued)

OTHER PUBLICATIONS

Extended European Search Report dated Oct. 19, 2021 for Application No. 19757833.9.
(Continued)

*Primary Examiner* — Tuyen Tra
(74) *Attorney, Agent, or Firm* — McCarter & English, LLP

(57) ABSTRACT

A system, method, and non-transitory computer readable medium for providing a visual examination are provided. A diagnostic module configured to execute on a first computing device communicatively coupled to a head mounted holographic display device worn by a user renders a virtual arrangement displayed within the head mounted holographic display device at an initial simulated distance away from the user. Within the virtual arrangement is an imbedded pattern. A second computing device receives, from leads attached to the user, brain waves of the user. The second computing device displays a visual evoked potential within the brain waves. The visual evoked potential comprises an indication that the user visually identified the imbedded pattern at a second simulated distance away from the user. The visual evoked potential occurs at a focal length of a refractive error of an eye of the user.

20 Claims, 11 Drawing Sheets

Related U.S. Application Data is a continuation-in-part of application No. 15/904,995, filed on Feb. 26, 2018, now Pat. No. 10,441,161.

(58) Field of Classification Search
USPC .................................. 351/200, 222, 223
See application file for complete search history.

(56) References Cited

U.S. PATENT DOCUMENTS

| | | | |
|---|---|---|---|
| 10,371,946 | B2 | 8/2019 | Samec et al. |
| 10,441,161 | B2 | 10/2019 | Padula et al. |
| 2003/0048495 | A1 | 3/2003 | Vertoprakhov |
| 2013/0201446 | A1* | 8/2013 | Hall .................. G01M 11/0207 351/239 |
| 2016/0045388 | A1* | 2/2016 | Krenik .................. A61B 3/024 351/203 |
| 2016/0192858 | A1* | 7/2016 | Min ........................ A61B 5/375 600/545 |
| 2017/0000326 | A1 | 1/2017 | Samec et al. |

FOREIGN PATENT DOCUMENTS

| | | |
|---|---|---|
| CN | 107592798 A | 1/2018 |
| DE | 3405778 A1 | 8/1985 |
| JP | H10134525 | 5/1998 |
| JP | H1173672 | 3/1999 |
| JP | 2001025904 | 1/2001 |
| JP | 2015-006425 | 1/2015 |
| JP | 2016-535872 | 11/2016 |
| WO | WO 2015/032828 | 3/2015 |
| WO | 2019/156485 A1 | 8/2019 |

OTHER PUBLICATIONS

U.S. Appl. No. 15/904,995, filed Feb. 26, 2018, U.S. Pat. No. 10,441,161.
PCT/US2019/019251, filed Feb. 22, 2019, WO 2019/165280.
U.S. Appl. No. 16/593,619, filed Oct. 4, 2019, US 2020/0113434 A1.
U.S. Appl. No. 16/923,672, filed Jul. 8, 2020, US 2020/0409153 A1.
Eye Focus, Vision Testing with a Hologram, Holographic Technology. Retrieved online at: http://www.eyefocus.com.au/common/node/10. 7 pages. Jan. 2011.
Hubel et al., Receptive fields of single neurones in the cat's striate cortex. J Physiol. Oct. 1959;148(3):574-91.
Liebowitz, The two modes of processing concept and some implications. Organization and Representation in Perception. Jacob Beck (Ed.), Lawrence Erlbaum Associates, Hillsdale, New Jersey. Chapter 17, pp. 343-363. (1982).
Padula et al., Evaluating and treating visual dysfunction. Brain Injury Medicine. Zasler (Ed.), Demos Medical Publishing. pp. 511-528, (2007).
Padula et al., Visual evoked potentials (VEP) evaluating treatment for post-trauma vision syndrome (PTVS) in patients with traumatic brain injuries (TBI). Brain Inj. Feb.-Mar. 1994;8(2):125-33.
Trevarthen, Two mechanisms of vision in primates. Psychol Forsch. 1968;31(4):299-348.
Avudainayagam et al., A Test for Progressive Myopia and the Role of Latent Accommodation in its Development, International Journal of Ophthalmology and Clinical Research, 2015, 2:2, published Apr. 10, 2015.
English Translation of Japanese Office Action dated Jun. 7, 2022 for Japanese Patent Application No. 2020-567445.

* cited by examiner

HOLOGRAPHIC REAL SPACE REFRACTIVE SYSTEM

CROSS-REFERENCE TO RELATED APPLICATION

This application is a continuation-in-part of U.S. patent application Ser. No. 15/904,995, filed on Feb. 26, 2018, and now issued as U.S. Pat. No. 10,441,161, and U.S. patent application Ser. No. 16/593,619, filed on Oct. 4, 2019. The prior applications are incorporated herein by reference in their entirety.

BACKGROUND

1. Technical Field

Systems and methods for providing a visual examination using holographic projection in real space and time are provided.

2. Background Art

For over one hundred years, doctors have provided eye examinations including refraction by using lenses and prisms to determine the refractive state and binocularity of the patient. Refraction means to bend light. Persons with myopia (nearsightedness), hyperopia (farsightedness), and astigmatism (two different power curves) performed a refraction to correct the refractive state and blurred vision of the patient by using physical lenses and prisms. While in the 19th century the refraction was mostly conducted with a trial frame by holding up individual lenses before each eye to make the image more clear, in the 20th century the phoropter (meaning "many lenses") was developed. This instrument was extended on the arm of a physical stand and the instrument was positioned before the patient's face. The clinician would then turn the dial to move different lenses in front of the person's eyes to find the best subjective refraction to improve distance vision. The instrument was then advanced to include prisms that could be used to disassociate images or change the position of the image enabling the clinician the ability to evaluate muscle ranges and the ability to maintain eye alignment and binocularity. It also permitted assessment of the person's ability to accommodate or focus at a near range. This was all for the purpose of designing glasses to improve eyesight and visual acuity for both distance and near ranges as well as to prescribe prisms to correct for imbalance in eye alignment affecting binocularity.

Visual acuity and refraction are necessary for assessing vision and the prescription of corrective lenses for myopia (nearsightedness), hyperopia (farsightedness) and astigmatism. The standards for testing are to provide a visual acuity chart at a specified distance from the subject to measure the smallest resolution of detail that can be seen by each eye for a distance range. The Snellen Acuity chart was developed by an ophthalmologist, Herman Snellen MD, in 1862. The Snellen Acuity Chart is still used today in addition to other charts.

SUMMARY OF THE INVENTION

A method for providing a visual examination is provided. A diagnostic module configured to execute on a first computing device communicatively coupled to a head mounted holographic display device worn by a user renders a virtual arrangement displayed within the head mounted holographic display device at an initial simulated distance away from the user. The virtual arrangement comprises a background grid orientated in a first orientation and an imbedded pattern located within the background grid. The imbedded pattern is orientated in a second orientation that is different from the first orientation. The diagnostic module updates the rendering of the virtual arrangement within the head mounted holographic display device. The update comprises a virtual movement of the virtual arrangement. A second computing device receives, from leads attached to the user, brain waves of the user. The second computing device displays a visual evoked potential within the brain waves. The visual evoked potential comprises an indication that the user visually identifies the imbedded pattern at a second simulated distance away from the user. The visual evoked potential occurs at a focal length of a myopic correction of the user.

The virtual arrangement includes a background grid orientated in a first orientation and an imbedded pattern located within the background grid. The imbedded pattern is orientated in a second orientation that is different from the first orientation. For example, the background grid and the imbedded pattern are patterns of lines that subtend a specific minute of arc separation between the lines. In an exemplary embodiment, the background grid is a pattern of lines of a minute of arc and the imbedded pattern is a geometric shape imbedded within the background grid, where the imbedded pattern is a pattern of lines of the same minute of arc as the virtual arrangement but in an opposing direction to create the geometric shape. Some of the lines of the imbedded pattern may be positioned at an opposite angle to the lines in the background grid.

A system for providing a visual examination is provided. The system includes a head mounted holographic display device, a first computing device communicatively coupled to the head mounted holographic display device worn by a user and a diagnostic module configured to execute on the first computing device. The diagnostic module when executed renders a virtual arrangement displayed within the head mounted holographic display device at an initial simulated distance away from the user, wherein the virtual arrangement comprises a background grid orientated in a first orientation and an imbedded pattern located within the background grid orientated in a second orientation that is different from the first orientation. The diagnostic module when executed further updates the rendering of the virtual arrangement within the head mounted holographic display device, wherein the update comprises a virtual movement of the virtual arrangement. The system further includes a second computing device coupled to leads attached to the user. The second computing device when executed receives, from the leads attached to the user, brain waves of the user, and displays a visual evoked potential within the brain waves. The visual evoked potential comprises an indication that the user visually identified the imbedded pattern within the virtual arrangement at a second simulated distance away from the user. The visual evoked potential occurs at a focal length of a myopic correction of the user.

A non-transitory computer readable medium storing instructions executable by a processing device is provided. Execution of the instructions causes the processing device to implement a method for providing a visual examination. The method comprises rendering, via a diagnostic module configured to execute on a first computing device communicatively coupled to a head mounted holographic display device worn by a user, a virtual arrangement displayed within the head mounted holographic display device at an initial simulated distance away from the user. The virtual arrangement comprises a background grid orientated in a first orientation and an imbedded pattern located within the background grid orientated in a second orientation that is different from the first orientation. The method further comprises updating, via the diagnostic module, the rendering of the virtual arrangement within the head mounted holographic display device, wherein the update comprises a virtual movement of the virtual arrangement. The method also comprises receiving, by a second computing device from leads attached to the user, brain waves of the user. The method further comprises displaying, via the second computing device, a visual evoked potential within the brain waves. The visual evoked potential comprises an indication that the user visually identified the imbedded pattern within the virtual arrangement at a second simulated distance away from the user. The visual evoked potential occurs at a focal length of a myopic correction of the user.

Additional features, functions and benefits of the disclosed systems and methods will be apparent from the detailed description which follows, particularly when read in conjunction with the accompanying figures.

BRIEF DESCRIPTION OF DRAWINGS

Illustrative embodiments are shown by way of example in the accompanying drawings and should not be considered as a limitation of the present disclosure.

DETAILED DESCRIPTION

Figure 1:
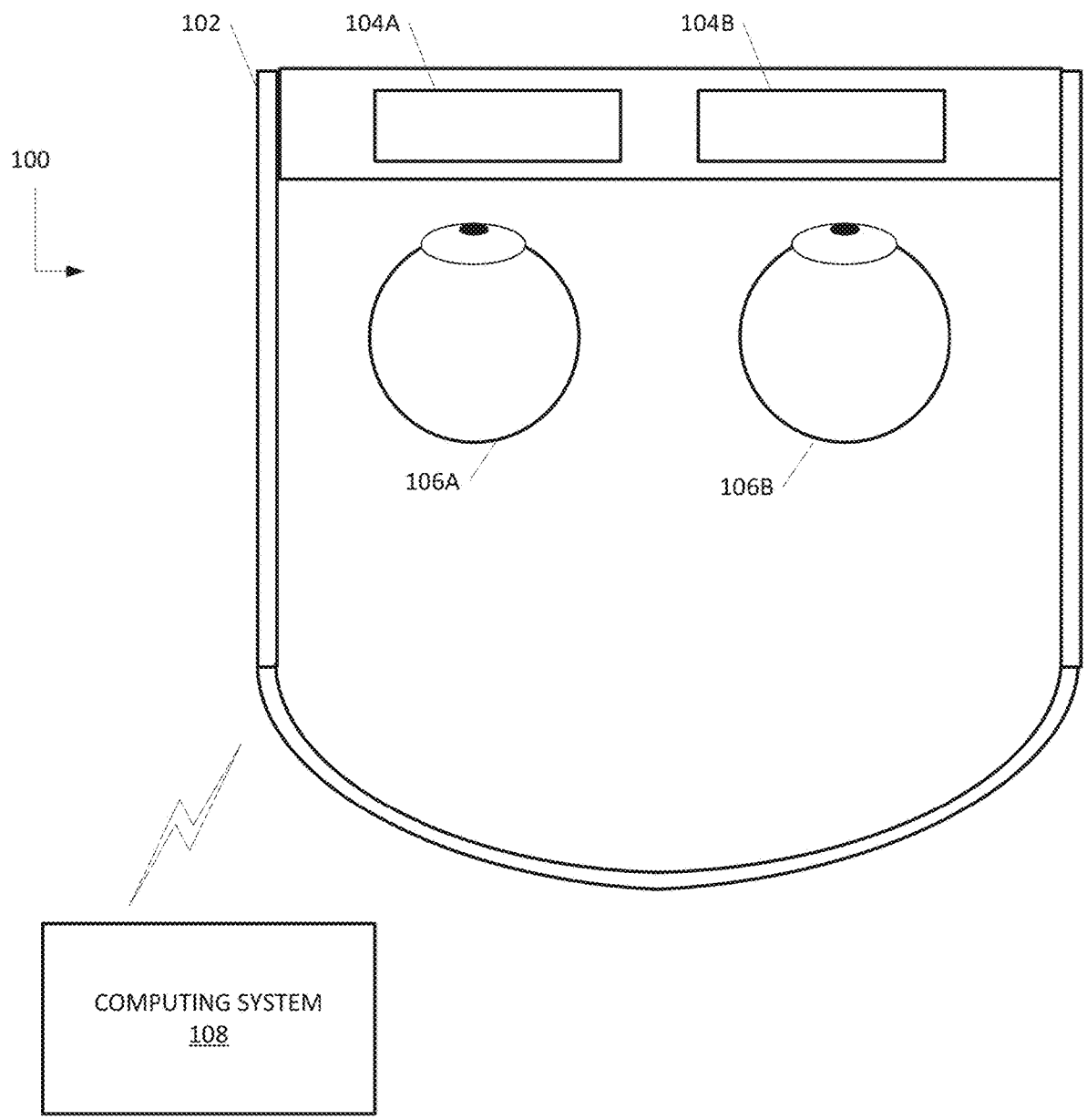
FIG. 1 is a block diagram illustrating a system for the holographic vision testing device according to an exemplary embodiment.

Systems, methods, apparatus, and non-transitory computer readable medium are described for holographic eye testing to assess visual acuity and perform a refraction test. Example embodiments provide a device for utilizing virtual and/or augmentative holographic projections to perform eye testing, diagnosis, and prescriptive remedy. In some embodiments, a disclosed holographic vision testing device renders on a head mounted device, at least one two-dimensional (2D) or three-dimensional (3D) virtual arrangement within the holographic display device. The rendering of the virtual arrangement corresponds to a virtual level of depth viewable by a user wearing the head mounted device.

In an exemplary embodiment, the virtual arrangement includes a background grid comprising a series of lines in a same or similar orientation. The series of lines of the background grid subtends x minutes of arc with a spacing of y minute of arc, where x and y are predefined numbers of minutes of arc. In an exemplary embodiment, the series of lines subtend 5 minutes of arc with a spacing of 1 minute of arc. Different minutes of arc may be used in other embodiments. Within the background grid is an imbedded pattern that is in a different orientation from the background grid. For example, the imbedded pattern may be a series of lines of the same minute of arc as the background grid but that are in a different orientation from the background grid to create a geometric shape or form. The imbedded pattern forms the geometric shape, such as, but not limited to, a checkerboard, a circle, or a diamond. Any universal geometric shape can be used as well, such as imbedded letters, numbers, shapes, and pictures that will be universal for different cultures and languages and that will not discriminate against age or literacy.

The holographic display device updates the rendering of the virtual arrangement. The update includes a virtual movement of the virtual arrangement within the virtual level of depth, typically closer or farther from the user.

A computing device coupled to a computing display and/or coupled to leads attached to the user receives brain waves of the user via the leads. For example, the computing device coupled to the leads may utilize an electroencephalogram (EEG) to detect and/or display the electrical activity in the brain of the user for monitoring for a visual evoked potential. Of primary interest is the latency of the positive wave at a midline occipital EEG electrode, usually at approximately 100 ms after stimulation, called the Visual Evoked Potential P-100. The computing device coupled to the leads displays waveforms on the computing display, including waveforms of a visual evoked potential. The visual evoked potential comprises an indication that the user visually identified the imbedded pattern within the background grid. The visual evoked potential occurs at a focal length of a myopic correction of the user. More specifically, at the focal length of a refractive error, pattern receptors respond causing the user to identify the imbedded pattern.

In some embodiments, the computing device coupled to the leads or a separate computing device identifies the Visual Evoked Potential P-100 (for example, using artificial intelligence or other appropriate software to identify the Visual Evoked Potential P-100 within the waveforms). In other embodiments, a human reviews the waveforms and identifies the Visual Evoked Potential P-100.

The disclosed systems, methods, apparatus, and non-transitory computer readable medium utilizes the virtual arrangement to assess refractive power or error of the eye by causing a response of pattern receptors at the focal length of the refractive error of the eye. This is accomplished by projecting the virtual arrangement via virtual or augmentative reality using the head mounted device. The formula for calculation of the refractive power of the eye is diopters=100 cm./focal length (cm.).

The user recognizes the imbedded pattern based on pattern receptors organizing and establishing visual imagery though the support of a bi-modal visual process. The pattern receptors in the visual cortex function by processing information delivered by responding to groups of cells in the retina that are stimulated by patterns and lines. The imbedded pattern stimulates pattern receptors of the user using the holographic vision testing device to trigger a response to the imbedded pattern to assess visual acuity and refraction. The imbedded pattern is only seen if the user can resolve the minutes of arc (in an example embodiment, 5 minutes of arc), thereby enabling the user to recognize the imbedded figure. If the virtual arrangement is rendered to appear too far from the user or is moved away from the user more than the pattern receptors of the user can resolve the dimensional change in the lines then the imbedded pattern is not seen. The farthest distance that the pattern receptors respond is related to the focal length of the refractive error. The imbedded pattern causes pattern receptors to respond when the resolution of the imbedded pattern is at the focal length of the refractive correction.

In an exemplary embodiment, the disclosed systems, methods, apparatus, and non-transitory computer readable medium can non-verbally assess visual acuity and/or the refractive state of an eye by assessing visual evoked potentials using brain wave testing, for example, using an EEG to detect, evaluate, and/or display the electrical activity in the brain of the user. This is especially useful for non-verbal persons (infants through adult). This assessment is accomplished by placing leads (typically, three leads) attached to a computing device onto a scalp of the user wearing the holographic vision testing device. A reference electrode is usually placed on the earlobe, the midline top of the head, or on the forehead. A ground electrode can be placed at any location. The virtual arrangement is rendered to slowly move toward the person as the person fixates on the virtual arrangement. When the imbedded pattern is appreciated, a Visual Evoked Potential P-100 response is produced. In other words, when the pattern receptors are triggered, a brain wave called the Visual Evoked Potential P-100 (or P-100) is released and this can be captured as a visual evoked potential (VEP). The distance from the person's eyes at the time the P-100 response is appreciated marks the focal length of the spherical refractive power of the eye. By determining the minutes of arc subtended by the lines on the chart producing the geometric form, an acuity measurement for this eye can be determined using the following formula: 1 minute of arc separation of a 5 minute subtented dimensional target=20/20 (feet) or 6/6 (meters) of resolution.

A minute of arc, arcminute (arcmin), arc minute, or minute arc is a unit of angular measurement equal to 160 of one degree. Since one degree is 1360 of a turn (or complete rotation), one minute of arc is 121600 of a turn. An angle subtended from the macula to the size and distance to the target viewed represents the minutes of arc. The best resolution for the normal eye is 20/20 or 6/6. This represents a 1 minute of arc subtended angle from the eye.

The disclosed systems, methods, apparatus, and non-transitory computer readable medium can be designed to utilize different sized virtual arraignments (e.g., different sized backgrounds grid and/or different sized imbedded patterns) that will assess varying acuity at specified distances by stimulating pattern receptor response. The virtual arrangement can be designed for distance, intermediate, and near ranges.

In some embodiments, the virtual arraignments can be rendered and updated in computing devices other than the head mounted holographic display device described herein. For example, the virtual arraignments can be rendered and updated on a non-head mounted computing display (for example, a desktop computer display, a wall-mounted computer display, a tablet, etc.). In some embodiments, the virtual arraignments can be rendered and updated in an internet browser on, for example, a tablet, a desktop display, and/or a laptop display.

In other embodiments, the virtual arraignments can be rendered and updated in a vision testing kiosk in which a user places the user's head within the kiosk to view a display configured to render and update a virtual arraignment (for example, the head mounted holographic display device is mounted and/or installed within the kiosk). These embodiments can be used to test for visual acuity and/or developing an internet refraction system, but are not limited to these tests.

In other embodiments, the virtual arraignments can be printed on charts (e.g., an eye chart).

In all the above embodiments, leads may be attached to the user to receives brain waves of the user, as described within this disclosure.

The disclosed systems, methods, apparatus, and non-transitory computer readable medium are useful for assessing visual acuity and/or refraction in non-verbal persons. The testing is independent of different cultures, languages, or ages. The disclosed systems, methods, apparatus, and non-transitory computer readable medium enables both subjective testing by the subject as well as objective response directly from brain waves associated with the visual response. The implication is that objective testing can be performed for refraction on non-verbal patients potentially from infancy to the end stages of life. In addition, the disclosed systems, methods, apparatus, and non-transitory computer readable medium can be adapted for use with visual habilitation and rehabilitation for providing therapy to improve binocular function and visual skills. The disclosed systems, methods, apparatus, and non-transitory computer readable medium can further have beneficial use for sports visual enhancement to improve visual skills as well as reaction time. Military and police may benefit for training advanced visual skills with recognition danger for reaction time and decision-making. In addition, compromise to the bi-modal visual process can occur following concussion, traumatic brain injury, or other neurological events that affect the spatial visual process. Thus, the disclosed systems, methods, apparatus, and non-transitory computer readable medium serve as a means to assess visual processing dysfunction following a concussion or neurological event affecting the bi-modal visual process.

In some embodiments, the disclosed systems, methods, apparatus, and non-transitory computer readable medium can perform the refraction by using lenses within a phoropter, a trial frame, or any method employing optics to improve the resolution of detail for correcting myopia, hyperopia, and astigmatism.

In one embodiment, the disclosed systems, methods, apparatus, and non-transitory computer readable medium tests for astigmatism using a virtual arrangement (typically in a spherical shape) presented to the user. An imbedded pattern of a straight line is located within the virtual arrangement. The user performs a cross cylinder test to determine the axis of the cylinder. In particular, the virtual arrangement is rotated about an axis. The refraction in the augmentative reality device uses the near to far axis from the eye(s) or 'z' axis to move the arrangement until it is at the focal length of the eye causing the pattern receptors to respond and simultaneously causing the user to see the imbedded pattern such as a circle. A second arrangement is introduced and an imbedded pattern is rotated until the lines are the clearest. This is the astigmatic axis. The arrangement is move away from the user and the lines are rotated 90 degrees. The arrangement is then brought toward the user until the lines appear clear. The delta between the lines at the greater distance that were first seen (focal length of the spherical power and the focal length of the 90 degree rotated lines) represents the cylindrical power of the astigmatism. The spherical power, cylindrical power, and axis are determined to complete the refraction. This test is described in detail in U.S. patent application Ser. No. 15/904,995, which is incorporated herein by reference in its entirety.

FIG. 1 is a block diagram illustrating a system 100 for the holographic vision testing device according to an exemplary embodiment. In one embodiment, the holographic vision testing device can include a head mounted display (HMD) 102. The HMD 102 can include a pair of combiner lenses 104A, 104B for rendering a virtual arrangement within a user's field of view (FOV). The combiner lenses 104A, 104B can be calibrated to the interpupillary distance from the user's eyes 106A, 106B. A computing system 108 can be connected to the combiner lenses 104A, 104B. The holographic vision testing device can be repositioned in any of the nine primary gaze positions as needed. These tests are built to run on technical platforms that can project 2D and/or 3D holographic images within a field of view provided by a wired or wireless headset. The HMD 102 can be connected to an adjustable, cushioned inner headband, which can tilt the combiner lenses 104A, 104B up and down, as well as forward and backward. To wear the unit, the user fits the HMD 102 on their head, using an adjustment wheel at the back of the headband to secure it around the crown, supporting and distributing the weight of the unit equally for comfort, before tilting the visor and combiner lenses 104A, 104B towards the front of the eyes.

The computing system 108 can be inclusive to the HMD 102, where the holographic vision testing device is a self-contained apparatus. The computing system 108 in the self contained apparatus can include additional power circuitry to provide electrical current to the parts of the computing system 108. Alternatively, the computing system 108 can be external to the HMD 102 and communicatively coupled either through wired or wireless communication channels to the HMD 102. Wired communication channels can include digital video transmission formats including High Definition Multimedia Interface (HDMI), DisplayPort™ (DisplayPort is a trademark of VESA of San Jose Calif., U.S.A.), or any other transmission format capable of propagating a video signal from the computing system 108 to the combiner lenses 104A, 104B. Additionally, the HMD 102 can include speakers or headphones for the presentation of instructional audio to the user during the holographic eye tests. In a wireless communication embodiment, the HMD 102 can include a wireless adapter capable of low latency high bandwidth applications, including but not limited to IEEE 802.11ad. The wireless adapter can interface with the computing system 108 for the transmission of low latency video to be displayed upon the combiner lenses 104, 104B.

Additionally the computing system 108 can include software for the manipulation and rendering of 2D and/or 3D virtual arrangements within a virtual space. The software can include both platform software to support any fundamental functionality of the HMD 102, such as motion tracking, input functionality, and eye tracking. Platform software can be implemented in a virtual reality (VR) framework, augmented reality (AR) framework, or mixed reality (MR) framework. Platform software to support the fundamental functionality can include but are not limited to SteamVR® (SteamVR is a registered trademark of the Valve Corporation, Seattle Wash., U.S.A) software development kit (SDK), Oculus® VR SDK (Oculus is a registered trademark of Oculus VR LLC, Irvine Calif., U.S.A.), OSVR (Open source VR) (OSVR is a registered trademark of Razer Asia Pacific Pte. Ltd. Singapore) SDK, and Microsoft Windows Mixed Reality Computing Platform. Application software executing on the computing system 108 with the underlying platform software can be a customized rendering engine, or an off-the-shelf 2D and/or 3D rendering framework, such as Unity® Software (Unity Software is a registered trademark of Unity Technologies of San Francisco Calif., U.S.A). The rendering framework can provide the basic building blocks of the virtualized environment for the holographic refractive eye test, including 3D objects and manipulation techniques to change the appearance of the 2D and/or 3D virtual arrangements. The rendering framework can provide application programming interfaces (APIs) for the instantiation of 2D and/or 3D virtual arrangements and well-defined interfaces for the manipulation of the 2D and/or 3D virtual arrangements within the framework. Common software programming language bindings for rendering frameworks include but are not limited to C++, Java, and C#. Additionally, the application software can provide settings to allow a test administrator to adjust actions within the test, such as holographic virtual arrangements speed and virtual arrangements orientations.

Figure 2:
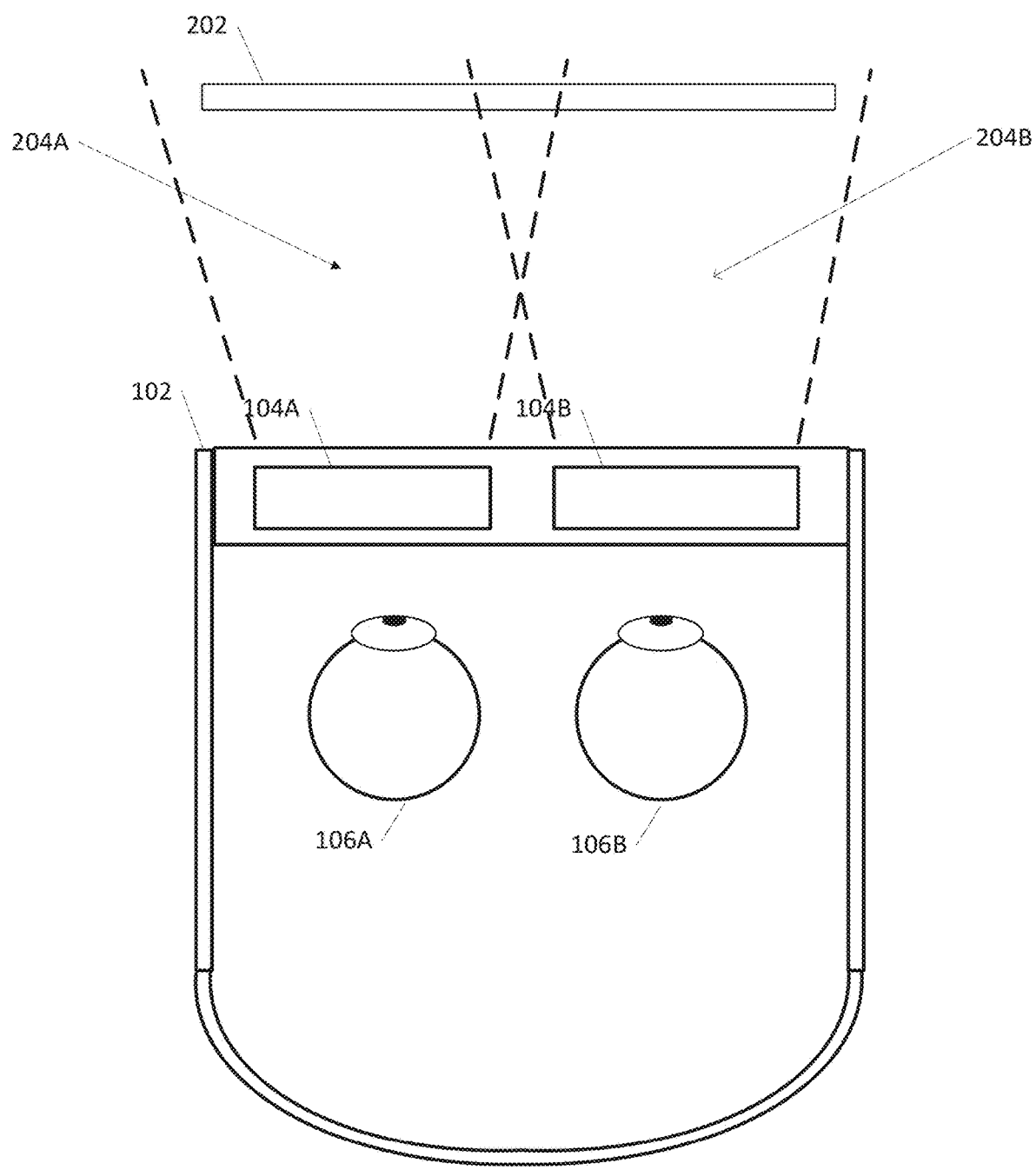
FIGS. 2 and 3 are diagrams illustrating a test for assessing visual acuity and performing refraction with a holographic vision testing device according to an exemplary embodiment.
Figure 3:
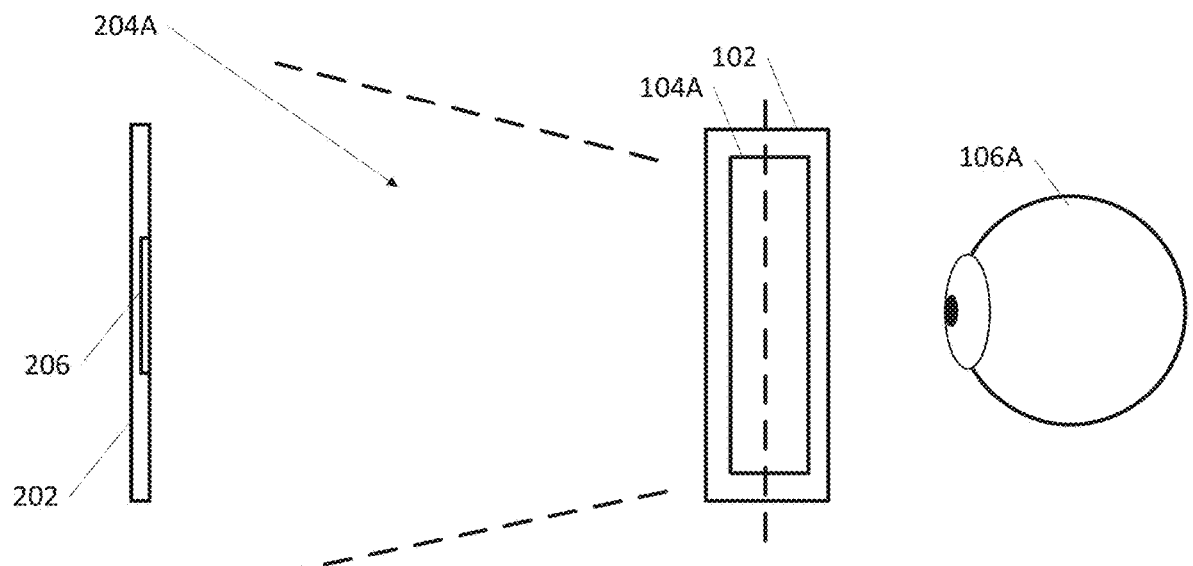

FIGS. 2 and 3 are diagrams illustrating a test for assessing visual acuity and performing refraction with a holographic vision testing device according to an exemplary embodiment. FIG. 2 is a side view of the holographic vision testing device and FIG. 3 is a top down view of the holographic vision testing device. In one embodiment, a virtual 2D or 3D virtual arrangement 202 can be manipulated in a user's field of view (FOV) 204A, 204B. The virtual arrangement 202 can have a starting point within the user's FOV 204A, 204B. Utilizing application software, the virtual arrangement 202 is translated and projected on the combiner lenses 104A, 104B to give the appearance that the virtual arrangement 202 is a set distance from the view of the user's eyes 106A, 106B. For example, in some embodiments, the presentation of the virtual arrangement 202 can correspond to projection of the virtual arrangement 202 at distances of 16 inches to 20 feet in front of the user's eyes 106A, 106B. The range of distances allows visual acuity to be measured at different intervals of depth for better confidence in results.

The virtual arrangement 202 is rendered moving towards or moving away from the user in the user's FOV 204A, 204B. A computing device may utilize an electroencephalogram (EEG) to detect, evaluate, and display the electrical activity in the brain of the user. For example, responses are recorded from electrodes that are placed on the back of the user's head and are observed as a reading on the EEG. A visual evoked potential is an evoked potential caused by a visual stimulus, such as the imbedded pattern 206. In the exemplary embodiment, the visual evoked potential comprises an indication that the user visually identified an imbedded pattern 206 within the virtual arrangement 202. The visual evoked potential occurs at a focal length of a myopic correction of the user. The power of any lens system that corrects myopia can be expressed in units called diopters (D), the reciprocal of its focal length in meters. The lens powers on an eyeglass prescription for myopia always begin with a minus sign. The higher the power number of the lens, the more myopia it corrects.

In some embodiments, the user can provide input to the application software or platform software. The input can take the form of voice commands, gestures, or input from a "clicker." For example, at the point in which the imbedded pattern 206 becomes clear to the user, the user can provide input to stop any motion or translation of the virtual arrangement 202. The application software evaluates a delta (or change) between the midpoint of the user's FOV 204A, 204B and the point at which the virtual arrangement 202 were located when the user provided input to stop the motion or translation. The delta can be represented as a deviation relative to the virtual distance of the virtual arrangement 202 from the patient. A diopter is measured by the deviation of the image at a specific virtual distance (1 prism diopter=1 virtual cm deviation of the image at a 1 virtual meter distance).

In one embodiment, the user can start the test by providing input to the computing system 108. The input can take the form of voice commands, including saying key words indicative of beginning the test, gestures or providing input from a "clicker." The user states the word "start" to begin the test. As the test begins, the virtual arrangement 202 is translated toward the combiner lenses 104A, 104B to give the user the appearance that the virtual arrangement 202 is coming directly at the user's eyes 106A, 106B.

In some embodiment, when the user can see the imbedded pattern 206 clearly, the user can provide input to stop the test in the form of a voice command of "stop." The computing system 108 ceases translation of the virtual arrangement 202 and calculates a delta distance from the starting point of the virtual arrangement 202 to the point where the virtual arrangement 202 resides at the end of the test. A constant point of reference on the virtual arrangement 202 can be utilized to determine a consistent location to determine the delta distance.

In some embodiments, the virtual arrangement 202 can be moved forward or backwards. Control of the test can take the form voice commands including "forward" and "backward." A voice command of "forward" translates the plane 608, and associated virtual arrangement 202 toward the combiner lenses 104A, 104B. A voice command of "backward" translates the plane 608, and associated virtual arrangement 202 away from the combiner lenses 104A, 104B. Utilizing the voice commands and associated translations, a user can manipulated the virtual arrangement 202 until the user can identify the imbedded pattern 206. The user can provide a voice command to the computing system 108, such as stating the word "stop" to complete the manipulation portion of the test. Upon the receipt of the "stop" command, the computing system 108 disallows subsequent input commands, such as "forward" and "backward," and determines a final distance of the virtual arrangement 202.

Figure 4A:
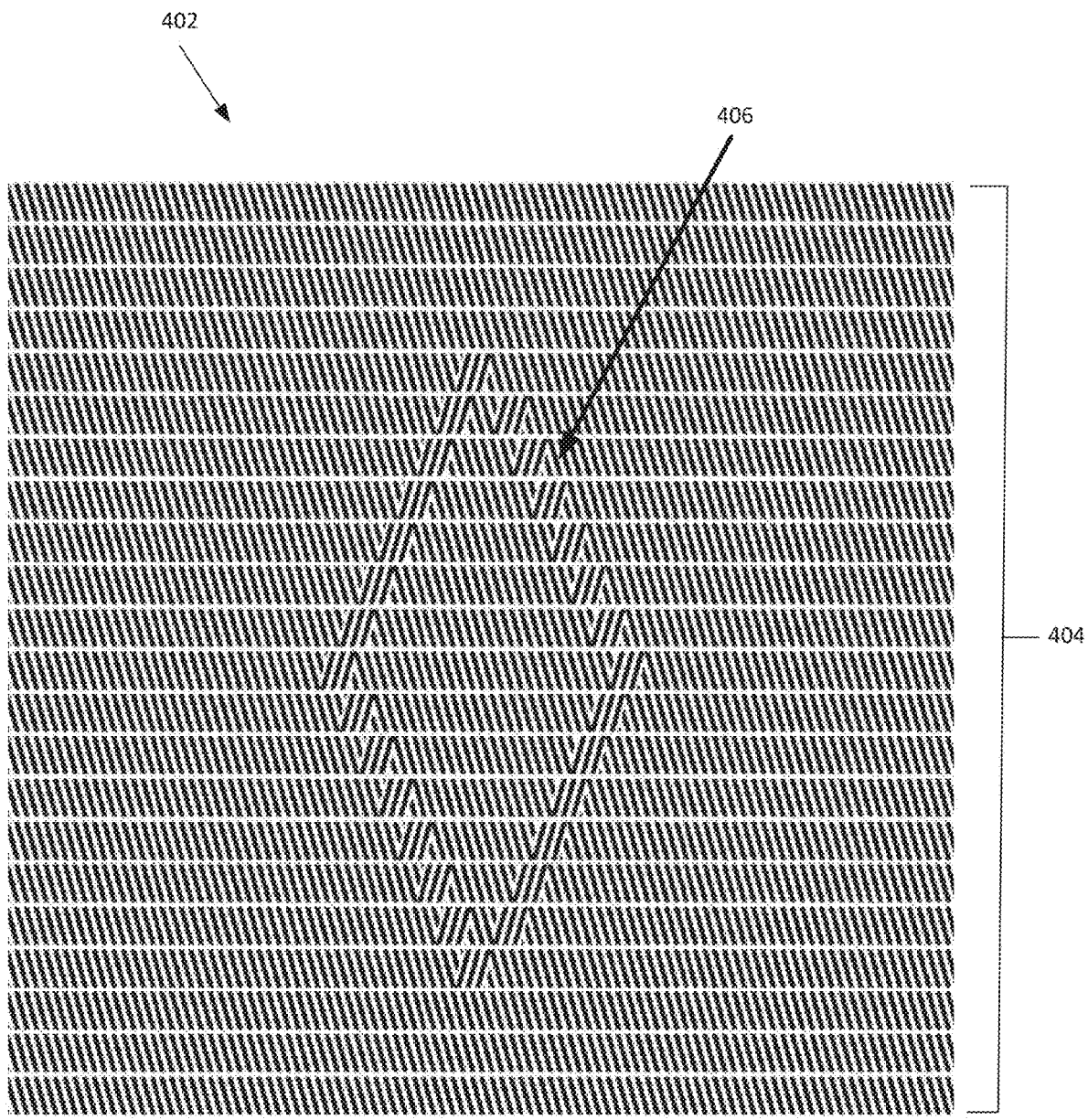
FIGS. 4A and 4B illustrate sample virtual arrangements in accordance with an exemplary embodiment.

FIG. 4A illustrates a sample virtual arrangement 402 in accordance with an exemplary embodiment. In an exemplary embodiment, the virtual arrangement 402 includes a background grid 404 of a series of lines that subtend 5 minutes of arc with a spacing of 1 minute of arc. The virtual arrangement 402 further includes an imbedded pattern 406 of lines that are not in the same orientation as the background grid 404. In this embodiment, the imbedded pattern 406 forms a diamond, although in different embodiments different patterns may be formed. The imbedded pattern 406 stimulates a certain group(s) of pattern receptors to trigger a response to the imbedded pattern 406 (here, a diamond). The imbedded pattern 406 is only seen if the person can resolve the 5 minutes of arc thereby enabling the person to recognize the imbedded pattern 406 of the diamond. If the virtual arrangement 402 is located and/or moved a greater distance from the user more than the pattern receptors can resolve the dimensional change in the lines then the imbedded pattern 406 of the diamond is not seen. Any universal geometric form can be used as an imbedded pattern, such as letters, numbers, shapes, and pictures that will be universal for different cultures and languages and that will not discriminate against age or literacy.

Figure 4B:
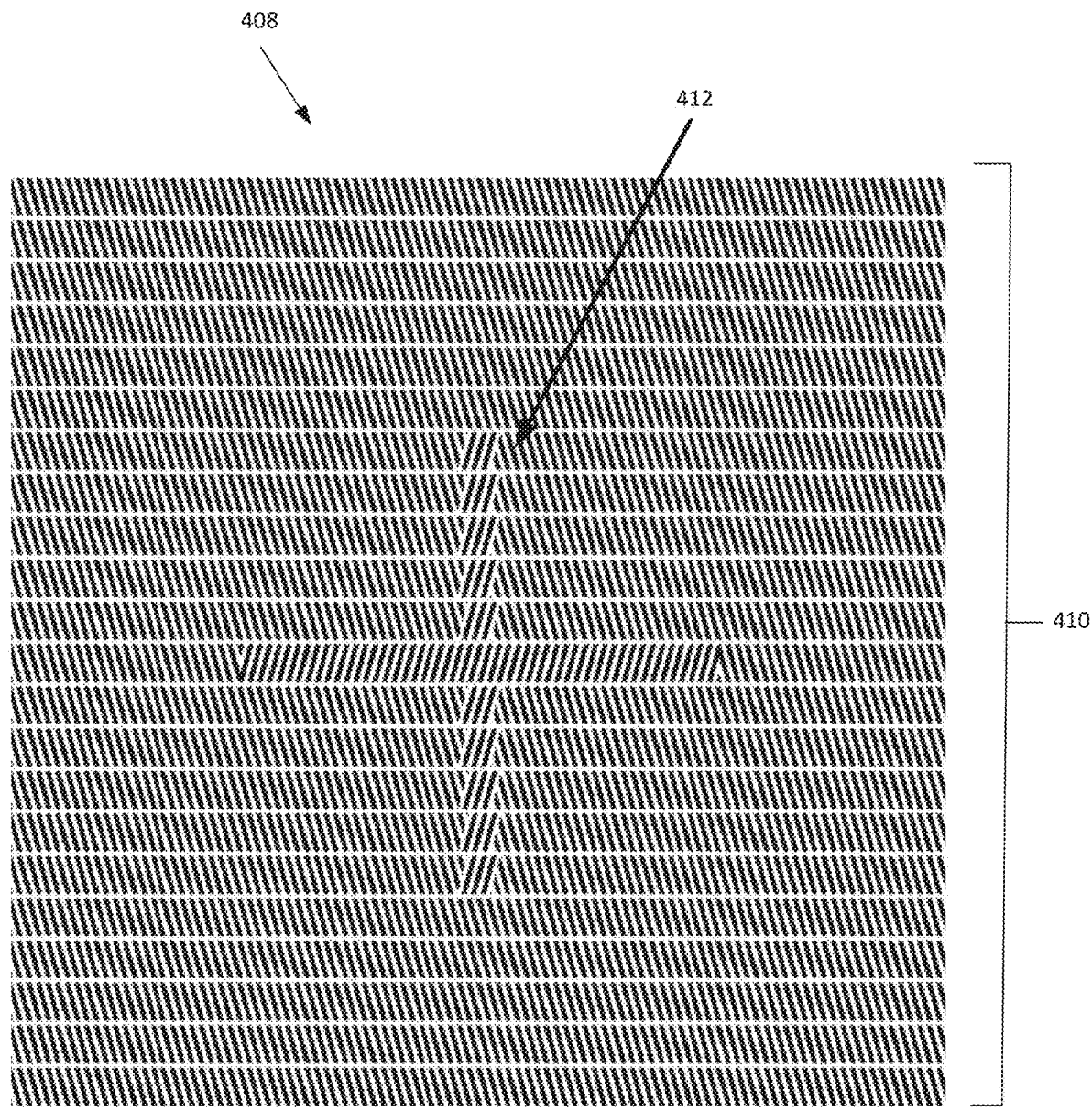

FIG. 4B illustrates another sample virtual arrangement 408 in accordance with an exemplary embodiment. In an exemplary embodiment, the virtual arrangement 408 includes with a background grid 410 of a series of lines that subtend 5 minutes of arc with a spacing of 1 minute of arc. The virtual arrangement 408 further includes an imbedded pattern 412 of lines (here, forming a cross) that are not in the same orientation as the background grid 410.

Figure 5A:
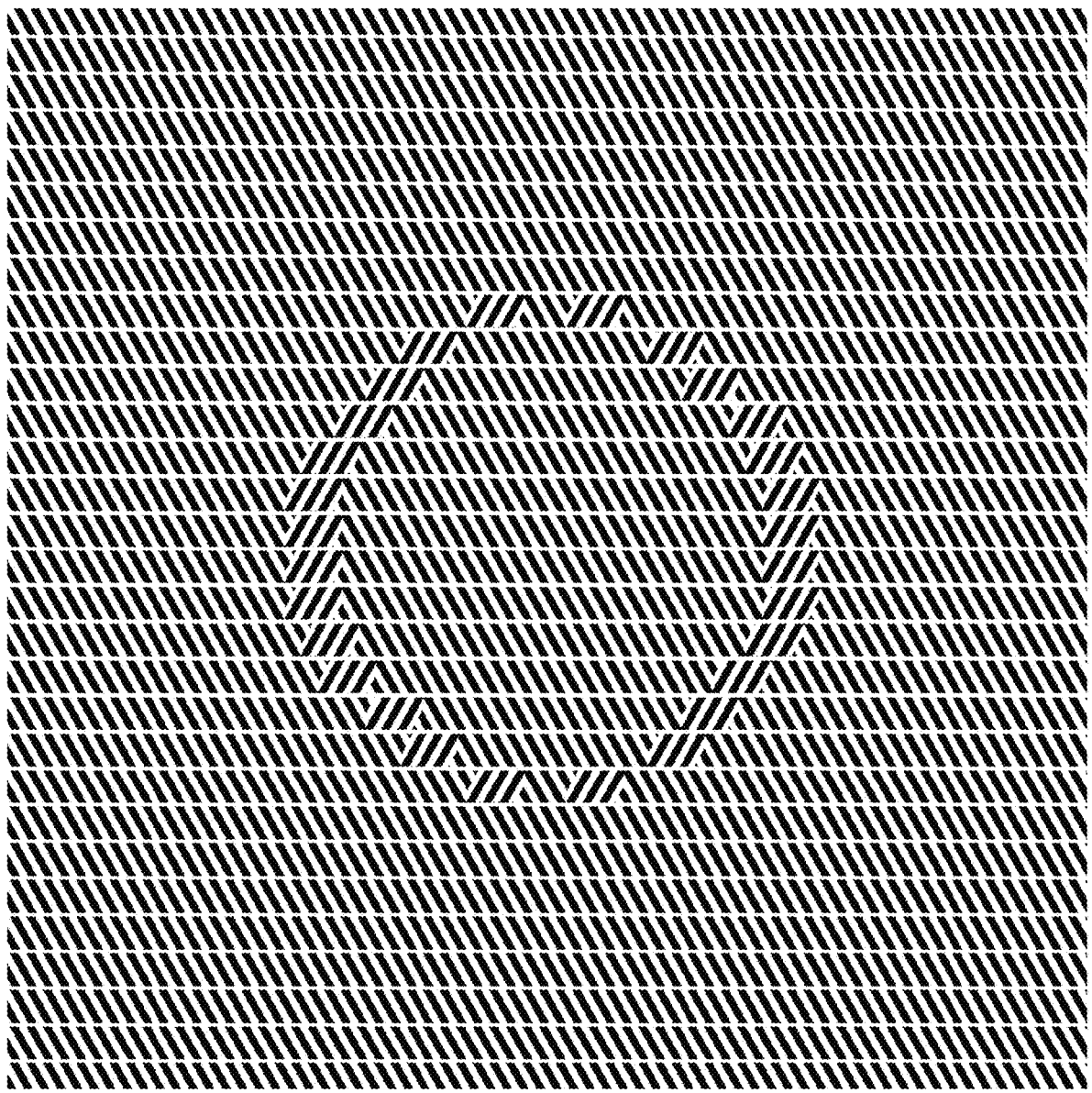
FIGS. 5A and 5B illustrate additional sample virtual arrangements in accordance with an exemplary embodiment.
Figure 5B:
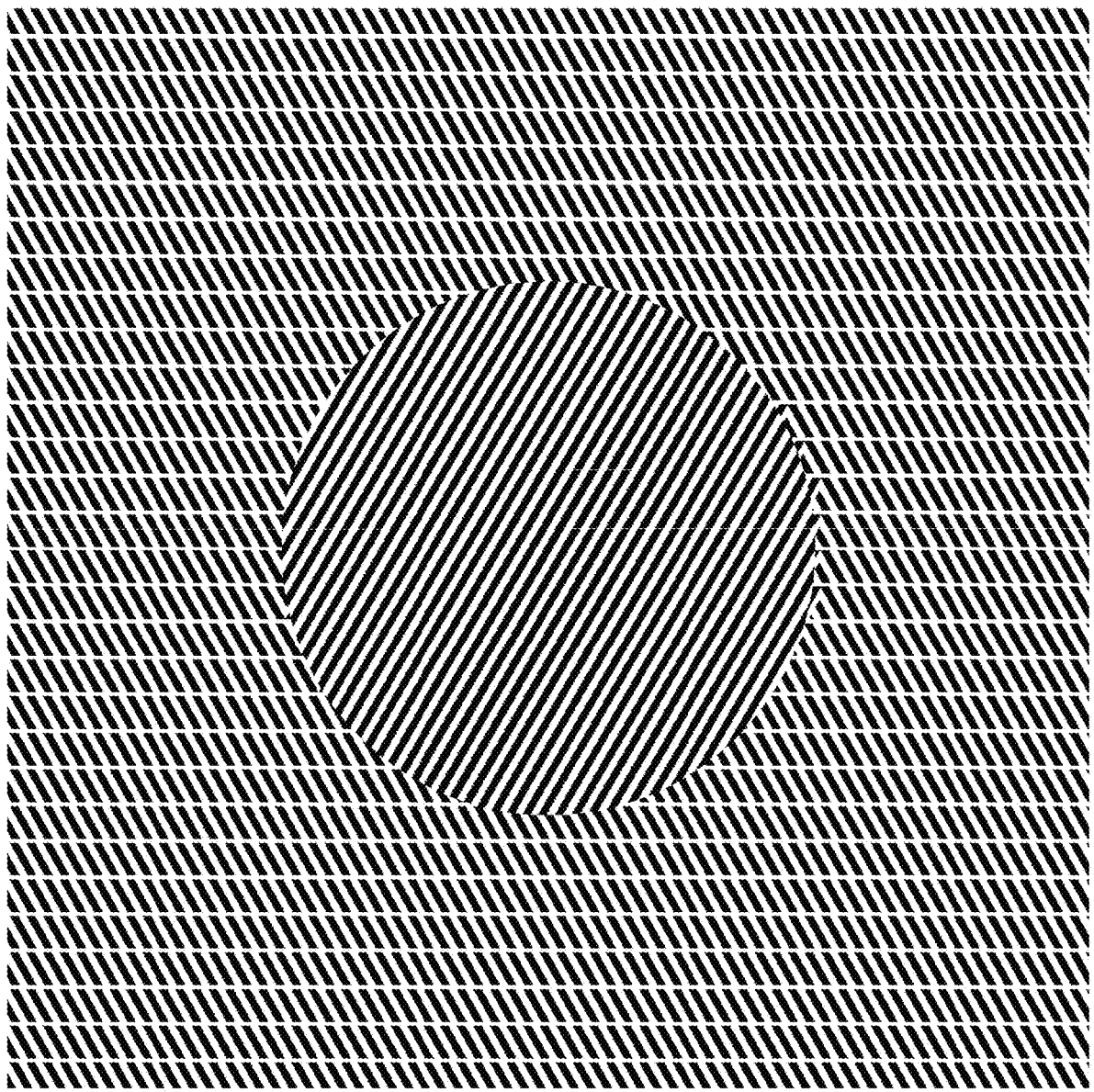

FIGS. 5A and 5B illustrate additional sample virtual arrangements in accordance with an exemplary embodiment.

In some embodiments, the virtual arraignments illustrated in FIGS. 4A, 4B, 5A, and 5B can be rendered and updated in computing devices other than the head mounted holographic display device described herein. For example, the virtual arraignments can be rendered and updated on non-head mounted computer displays, such as on desktop displays and/or laptop displays. In other embodiments, the virtual arraignments can be rendered and updated in a vision-testing kiosk in which a user places the user's head within the kiosk to view a virtual arraignment (for example, the described head mounted holographic display device is mounted and/or installed within the kiosk). These embodiments can be used to test, for example, but not limited to, visual acuity and/or developing an internet refraction system.

Figure 6:
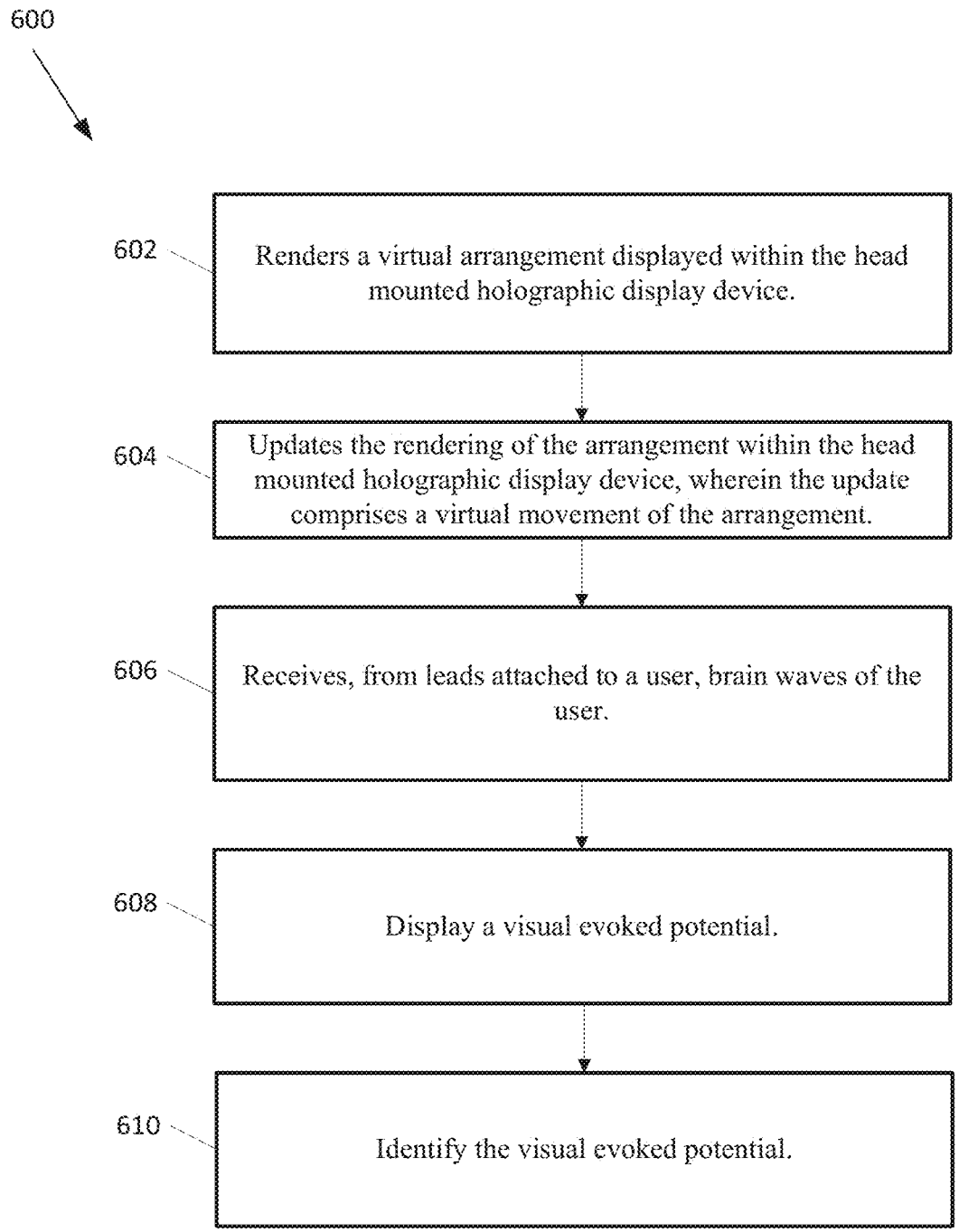
FIG. 6 illustrates a method for providing a visual examination in accordance with an exemplary embodiment.

FIG. 6 illustrates a method for providing a visual examination in accordance with an exemplary embodiment.

At step 602, a diagnostic module configured to execute on a first computing device communicatively coupled to a head mounted holographic display device renders a virtual arrangement displayed within the head mounted holographic display device. The virtual arrangement comprises a background grid orientated in a first orientation and an imbedded pattern located within the background grid orientated in a second orientation that is different from the first orientation.

At step 604, the diagnostic module updates the rendering of the virtual arrangement within the head mounted holographic display device, wherein the update comprises a virtual movement of the virtual arrangement.

At step 606, a second computing device receives brain waves from leads attached to a user.

At step 608, the second computing device displays a visual evoked potential. The visual evoked potential comprises an indication that the user visually identifies the imbedded pattern. The visual evoked potential occurs at a focal length of a myopic correction of the user.

At step 610, the visual evoked potential is identified by a user or a computing device (e.g., the second computing device or a third computing device) using artificial intelligence.

Figure 7:
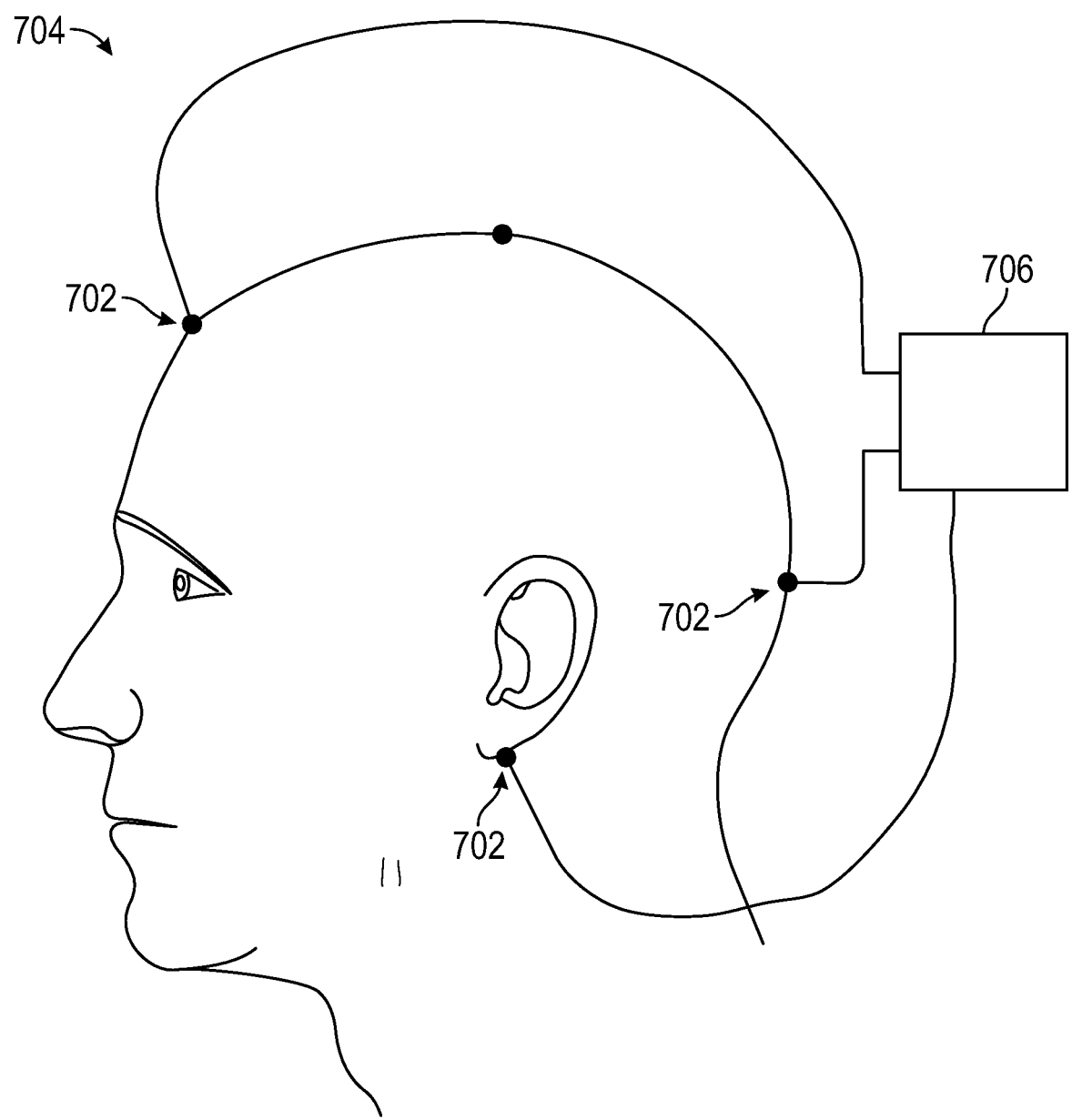
FIG. 7 depicts a diagram for evaluating the electrical activity in the brain of a user for monitoring a Visual Evoked Potential P-100 pattern response for a right (OD) eye and a left (OS) eye of the user using a virtual arrangement as a stimulus for fixation.

FIG. 7 depicts a diagram for evaluating the electrical activity in a brain of a user 704 for monitoring a Visual Evoked Potential P-100 pattern response for the user 704 provoked using a virtual arrangement (such as shown in FIGS. 4A-4B or FIGS. 5A-5B) as a stimulus for fixation, in accordance with an exemplary embodiment. The exemplary embodiment can non-verbally assess visual acuity and/or the refractive state of an eye by assessing visual evoked potentials using the brain wave testing, for example using an electroencephalogram (EEG) to detect and evaluate the electrical activity in the brain of the user. This assessment is accomplished by placing leads (typically, three leads)

attached to a computing device onto a scalp of the user using the holographic vision testing device. A reference electrode is usually placed on the earlobe, the midline top of the head, or on the forehead. A ground electrode can be placed at any location.

As shown, three leads 702 (via wires) are attached to the scalp of the user 704 for recording electrical activity in the brain, including a P-100 visual evoked potential. The three leads 702 are attached to a computing device 706 with software to be sensitive to changes in brain waves of the user 704 produced by visual awareness (visual evoked potential) of an imbedded pattern in the virtual arrangement.

In an exemplary embodiment, the virtual arrangement slowly moves toward the user as the user fixates on the virtual arrangement. When the imbedded pattern is appreciated, a P-100 response is produced. The distance from the user's eyes at the time the P-100 response is appreciated marks the focal length of the spherical refractive power of the eye. By determining the minutes of arc subtended by the lines on the chart producing the geometric form, an acuity measurement for this eye can also be determined using the following formula: 1 minute of arc separation of a 5 minute subtended dimensional target=20/20 (feet) or 6/6 (meters) of resolution.

Figure 8:
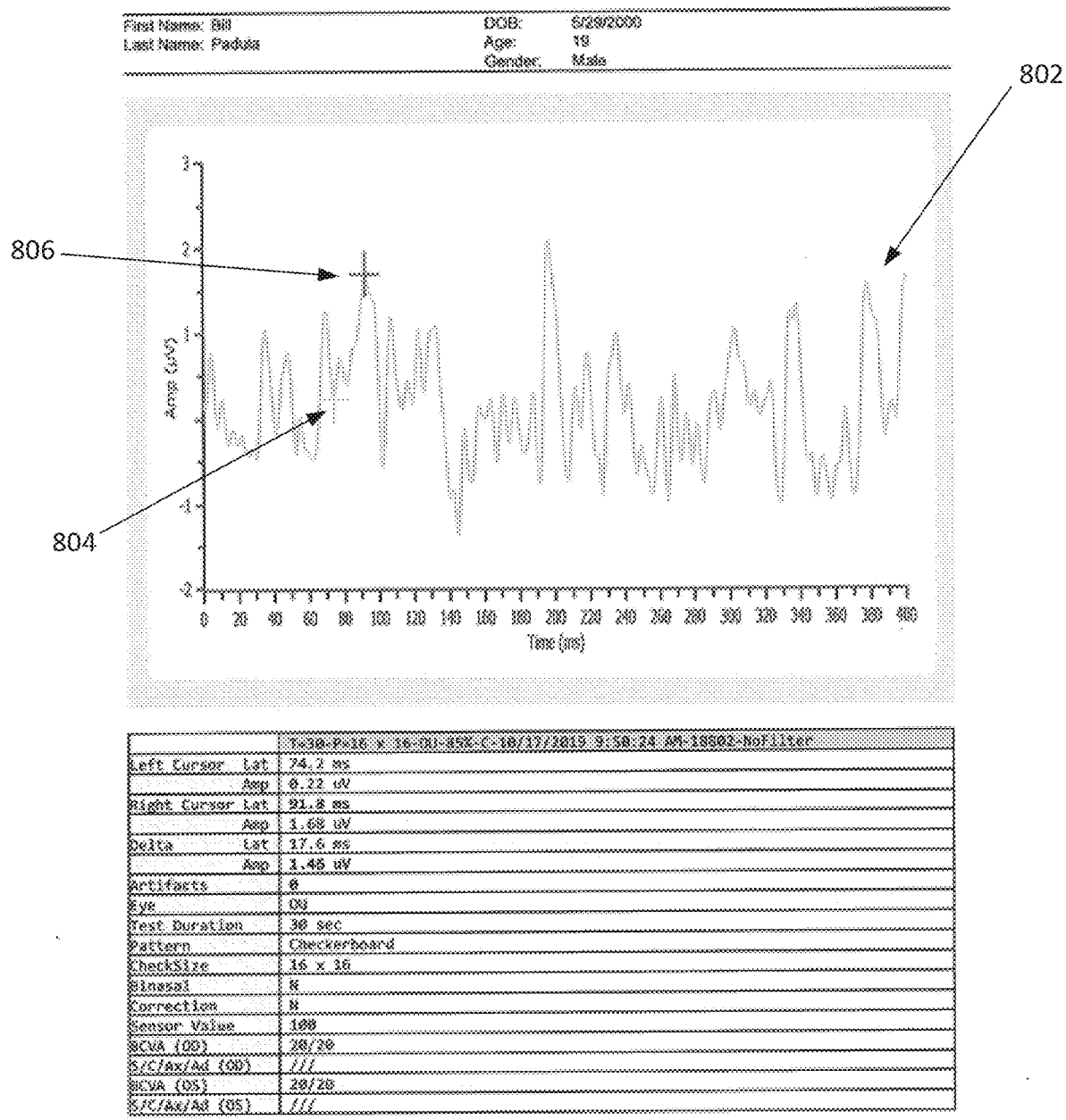
FIG. 8 illustrates exemplary electrical activity in the brain of a user in response to an imbedded pattern for a right (OD) eye and a left (OS) eye of a user using a virtual arrangement as described herein as a stimulus for fixation.

FIG. 8 illustrates exemplary electrical activity 802 in a brain of a user in response to viewing a virtual arrangement as described herein as a stimulus for fixation. A visual evoked potential (VEP) is primarily a relatively large, positive polarity wave generated in the occipital cortex in response to visual stimulation. It measures the conduction time of neuronal activity from the retina to the occipital cortex and is used clinically as a measure of the integrity and function of that pathway. Of primary interest is the latency of the positive wave at a midline occipital EEG electrode, usually at approximately 100 ms after stimulation, called the Visual Evoked Potential P-100. As described, the Visual Evoked Potential P-100 is elicited by an imbedded pattern that occurs at the focal length of the refractive error.

The illustrated electrical activity 802 was produced by having leads attached to the scalp of the user, as illustrated in FIG. 7. The leads are attached to a computing device with software to be sensitive to changes in brain waves of the user produced by visual awareness (visual evoked potential) of the user.

The electrical activity 802 is produced as the user views a virtual arrangement (for example, a virtual arrangement with an imbedded pattern of a checkerboard or circle) at a predefined virtual distance (for example, here virtually rendered at a six meters (twenty feet) distance). As the virtual arrangement with the imbedded pattern is rendered to move towards the user, pattern receptors respond in the visual process causing the user to see or identify the imbedded pattern at the focal length of the refractive error (in this example at 100 cm from the eye) when the pattern has lines that are 1 minute of arc separation. At this moment, a P-100 response is produced. This response coincided with it occurring at the focal length of the user's myopic correction, which is 100 centimeters. The formula for dioptric power is diopters=100 centimeters divided by focal length (centimeters).

In the illustration, the first cross 804 represents the beginning of the response from the pattern receptors and the second cross 806 represents the end of the response. Between the first cross 804 and the second cross 806 is the P-100 response. The x-axis represents a temporal period or a time period the response began and when it ended. The y-axis represents the amplitude of the response delivered form the bi-modal visual process in the brain.

The calculation determines that the subject has a −1.00 diopters of myopia and this corresponded to the subject's refractive correction that was determined by a refraction with a standard phoropter. The power of any lens system that corrects myopia can be expressed in diopters, the reciprocal of its focal length in meters.

If the user is myopic and the focal length is at a shorter distance than 6 meters the pattern receptors will not be able to see the subtended angle of the imbedded pattern so there will be no response until the pattern is moved toward the user or unless the user moves closer to the imbedded pattern to move it to the focal length of the refractive correction. A hyperopic eye can be given a plus lens to simulate closer focal lengths. When the subtended arc minute is resolved and the pattern receptors respond, the focal length is measured and the dioptric power is calculated. The testing lens is subtracted from this lens power to yield the dioptric power of the hyperopic eye.

Figure 9:
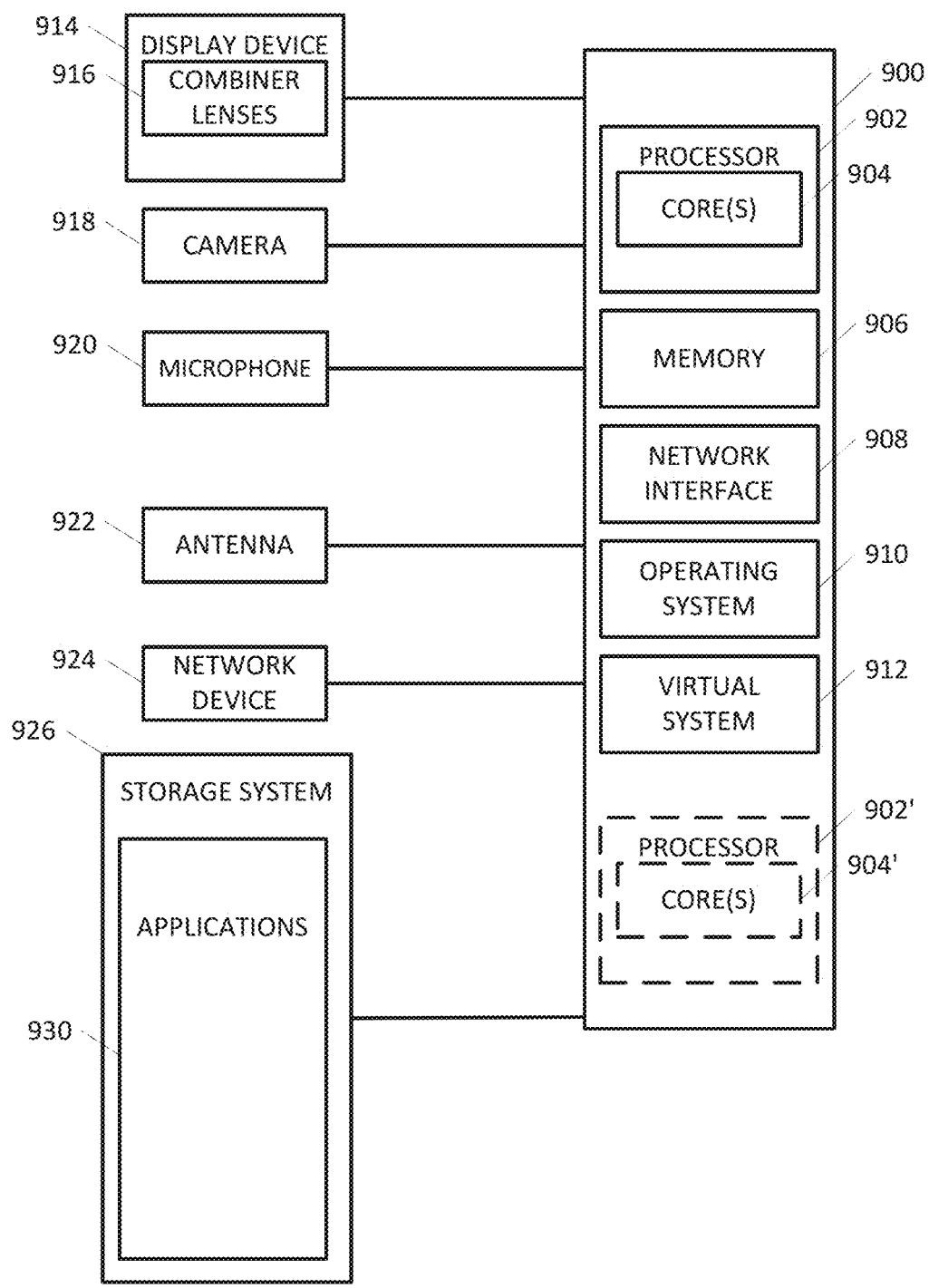
FIG. 9 depicts a block diagram an exemplary computing device in accordance with an exemplary embodiment.

FIG. 9 depicts a block diagram an exemplary computing device 900 in accordance with an exemplary embodiment. Computing device 900 may include computing device 108 for implementing the holographic vision testing device and/or computing device 706 for evaluating the electrical activity in the brain. For example, the computing device 900 can be embodied as a portion of the holographic vision testing device, and supporting computing devices. The computing device 900 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 906 included in the computing system 900 may store computer-readable and computer-executable instructions or software (e.g., applications 930 such as rendering application) for implementing exemplary operations of the computing device 900. The computing system 900 also includes configurable and/or programmable processor 902 and associated core(s) 904, and optionally, one or more additional configurable and/or programmable processor(s) 902' and associated core(s) 904' (for example, in the case of computer systems having multiple processors/cores), for executing computer-readable and computer-executable instructions or software stored in the memory 906 and other programs for implementing exemplary embodiments of the present disclosure. Processor 902 and processor(s) 902' may each be a single core processor or multiple core (904 and 904') processor. Either or both of processor 902 and processor(s) 902' may be configured to execute one or more of the instructions described in connection with computing system 900.

Virtualization may be employed in the computing system 900 so that infrastructure and resources in the computing system 900 may be shared dynamically. A virtual machine 912 may be provided to handle a process running on multiple processors so that the process appears to be using only one computing resource rather than multiple computing resources. Multiple virtual machines may also be used with one processor.

Memory 906 may include a computer system memory or random access memory, such as DRAM, SRAM, EDO RAM, and the like. Memory 906 may include other types of memory as well, or combinations thereof. The computing system 900 can receive data from input/output devices. A user may interact with the computing system 900 through a visual display device 914, such as a combiner lenses 916, which may display one or more virtual graphical user interfaces, a microphone 920 and one or more cameras 918.

The computing system 900 may also include one or more storage devices 926, such as a hard-drive, CD-ROM, or other computer readable media, for storing data and computer-readable instructions and/or software that implement exemplary embodiments of the present disclosure. For example, exemplary storage device 926 can include storing information associated with platform software and the application software.

The computing system 900 can include a network interface 908 configured to interface via one or more network devices 924 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing system can include one or more antennas 922 to facilitate wireless communication (e.g., via the network interface) between the computing system 900 and a network and/or between the computing system 900 and other computing devices. The network interface 908 may include a built-in network adapter, network interface card, PCMCIA network card, card bus network adapter, wireless network adapter, USB network adapter, modem or any other device suitable for interfacing the computing system 900 to any type of network capable of communication and performing the operations described herein.

The computing system 900 may run any operating system 910, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing system 900 and performing the operations described herein. In exemplary embodiments, the operating system 910 may be run in native mode or emulated mode. In an exemplary embodiment, the operating system 910 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes multiple system elements, device components, or method steps, those elements, components, or steps can be replaced with a single element, component, or step. Likewise, a single element, component, or step can be replaced with multiple elements, components, or steps that serve the same purpose. Moreover, while exemplary embodiments have been shown and described with references to particular embodiments thereof, those of ordinary skill in the art will understand that various substitutions and alterations in form and detail can be made therein without departing from the scope of the present disclosure. Further, still, other aspects, functions, and advantages are also within the scope of the present disclosure.

Exemplary flowcharts are provided herein for illustrative purposes and are non-limiting examples of methods. One of ordinary skill in the art will recognize that exemplary methods can include more or fewer steps than those illustrated in the exemplary flowcharts and that the steps in the exemplary flowcharts can be performed in a different order than the order shown in the illustrative flowcharts.

We claim:

1. A method for providing a visual examination, comprising:
    rendering, via a diagnostic module configured to execute on a first computing device communicatively coupled to a head mounted holographic display device worn by a user, a virtual arrangement displayed within the head mounted holographic display device at an initial simulated distance away from the user, wherein the virtual arrangement comprises a background grid orientated in a first orientation and an imbedded pattern located within the background grid orientated in a second orientation that is different from the first orientation;
    updating, via the diagnostic module, the rendering of the virtual arrangement within the head mounted holographic display device, wherein the update comprises a virtual movement of the virtual arrangement;
    receiving, by a second computing device from leads attached to the user, brain waves of the user;
    displaying, via the second computing device, a visual evoked potential within the brain waves, wherein the visual evoked potential comprises an indication that the user visually identified the imbedded pattern within the virtual arrangement at a second simulated distance away from the user,
    wherein the visual evoked potential occurs at a focal length of a refractive error of the user.

2. The method of claim 1, wherein the background grid comprises a series of lines in a same or similar orientation and the imbedded pattern comprises a series of lines that are in a different orientation from the series of lines of the background grid.

3. The method of claim 1, wherein the imbedded pattern forms a geometric form.

4. The method of claim 1, further comprising updating, via the diagnostic module, the rendering of the virtual arrangement within the holographic display device, wherein the updates comprises a virtual movement of the virtual arrangement towards the user.

5. The method of claim 1, further comprising generating, via the diagnostic module, a prescriptive remedy based on the focal length.

6. The method of claim 1, wherein the second computing device uses electroencephalogram to measure the brain waves.

7. The method of claim 1, further comprising identifying the visual evoked potential using artificial intelligence.

8. A system for providing a visual examination, comprising:
    a head mounted holographic display device;
    a first computing device communicatively coupled to the head mounted holographic display device worn by a user;
    a diagnostic module configured to execute on the first computing device, the diagnostic module when executed:
        renders a virtual arrangement displayed within the head mounted holographic display device at an initial simulated distance away from the user, wherein the virtual arrangement comprises a background grid orientated in a first orientation and an imbedded pattern located within the background grid orientated in a second orientation that is different from the first orientation, and updates the rendering of the virtual arrangement within the head mounted holographic display device, wherein the update comprises a virtual movement of the virtual arrangement; and a second computing device coupled to leads attached to the user, the second computing device when executed:

receives, from the leads attached to the user, brain waves of the user, and displays a visual evoked potential within the brain waves, wherein the visual evoked potential comprises an indication that the user visually identified the imbedded pattern within the virtual arrangement at a second simulated distance away from the user, wherein the visual evoked potential occurs at a focal length of a refractive error of the user.

9. The system of claim 8, wherein the background grid comprises a series of lines in a same or similar orientation and the imbedded pattern comprises a series of lines that are in a different orientation from the series of lines of the background grid.

10. The system of claim 8, wherein the imbedded pattern forms a geometric form.

11. The system of claim 8, further comprising updating, via the diagnostic module, the rendering of the virtual arrangement within the holographic display device, wherein the updates comprises a virtual movement of the virtual arrangement towards the user.

12. The system of claim 8, further comprising generating, via the diagnostic module, a prescriptive remedy based on the focal length.

13. The system of claim 8, wherein the second computing device uses electroencephalogram to measure the brain waves.

14. The system of claim 8, wherein the second computing device is configured to identify the visual evoked potential using artificial intelligence.

15. A non-transitory computer readable medium storing instructions executable by at least one processing device, wherein execution of the instructions causes the at least one processing device to implement a method for providing a visual examination, comprising:

rendering, via a diagnostic module configured to execute on a first computing device communicatively coupled to a head mounted holographic display device worn by a user, a virtual arrangement displayed within the head mounted holographic display device at an initial simulated distance away from the user, wherein the virtual arrangement comprises a background grid orientated in a first orientation and an imbedded pattern located within the background grid orientated in a second orientation that is different from the first orientation;

updating, via the diagnostic module, the rendering of the virtual arrangement within the head mounted holographic display device, wherein the update comprises a virtual movement of the virtual arrangement;

receiving, by a second computing device from leads attached to the user, brain waves of the user;

displaying, via the second computing device, a visual evoked potential within the brain waves, wherein the visual evoked potential comprises an indication that the user visually identified the imbedded pattern within the virtual arrangement at a second simulated distance away from the user, wherein the visual evoked potential occurs at a focal length of a refractive error of the user.

16. The non-transitory computer readable medium of claim 15, wherein the background grid comprises a series of lines in a same or similar orientation and the imbedded pattern comprises a series of lines that are in a different orientation from the series of lines of the background grid.

17. The non-transitory computer readable medium of claim 15, wherein the imbedded pattern forms a geometric form.

18. The non-transitory computer readable medium of claim 15, further comprising updating, via the diagnostic module, the rendering of the virtual arrangement within the holographic display device, wherein the updates comprises a virtual movement of the virtual arrangement towards the user.

19. The non-transitory computer readable medium of claim 15, further comprising generating, via the diagnostic module, a prescriptive remedy based on the focal length.

20. The non-transitory computer readable medium of claim 15, wherein the second computing device uses electroencephalogram to measure the brain waves.

* * * * *